United States Patent
Parthasarathy et al.

(10) Patent No.: US 7,347,976 B2
(45) Date of Patent: Mar. 25, 2008

(54) METHODS AND DEVICES FOR REMOVAL OF ORGANIC MOLECULES FROM BIOLOGICAL MIXTURES USING A HYDROPHILIC SOLID SUPPORT IN A HYDROPHOBIC MATRIX

(75) Inventors: Ranjani V. Parthasarathy, Woodbury, MN (US); Raj Rajagopal, Woodbury, MN (US); Vicky L. Morris, North Branch, MN (US); William Bedingham, Woodbury, MN (US); Barry W. Robole, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/027,226

(22) Filed: Dec. 20, 2001

(65) Prior Publication Data
US 2003/0120062 A1    Jun. 26, 2003

(51) Int. Cl.
*B01L 11/00*    (2006.01)
(52) U.S. Cl. ............... 422/101; 422/100; 422/102; 436/174; 436/175; 436/177; 436/178
(58) Field of Classification Search ............... 422/68.1, 422/99, 100, 101, 102, 103; 435/7.1, 7.2, 435/283.1, 287.1, 287.3, 287.7, 287.8, 287.9, 435/288.2, 288.4, 288.5; 426/161, 174, 175, 426/177, 178, 180
See application file for complete search history.

(56) References Cited

U.S. PATENT DOCUMENTS

| | | | |
|---|---|---|---|
| 3,157,635 A | 11/1964 | Tamaka et al. | 260/211.5 |
| 4,399,009 A * | 8/1983 | Chisholm | 204/98 |
| 4,399,235 A | 8/1983 | Raley, Jr. et al. | |
| 4,780,367 A | 10/1988 | Lau et al. | |
| 4,923,978 A | 5/1990 | McCormick | |
| 5,183,705 A | 2/1993 | Birkholz et al. | |
| 5,187,066 A | 2/1993 | Becker et al. | |
| 5,294,668 A | 3/1994 | Babu | |
| 5,334,316 A | 8/1994 | Bruening et al. | |
| 5,380,901 A | 1/1995 | Antonucci et al. | |
| 5,620,663 A | 4/1997 | Aysta et al. | |
| 5,633,290 A * | 5/1997 | Frechet et al. | 521/74 |
| 5,741,828 A | 4/1998 | Stoy et al. | |

(Continued)

FOREIGN PATENT DOCUMENTS

DE    197 31 670 A1    1/1999

(Continued)

OTHER PUBLICATIONS

"ABI Prism® BigDye™ Terminators v3.0 Cycle Sequencing Kit," product information [online]. Applied Biosystems, 2000, 2001 [retrieved Dec. 3, 2001]. Retrieved from the Internet: <URL:http://www.appliedbiosystems.com/products/productdetail.cfm?id=81>, 1 page.

(Continued)

*Primary Examiner*—Jill Warden
*Assistant Examiner*—Dwayne K Handy
(74) *Attorney, Agent, or Firm*—Ann M. Mueting (57) ABSTRACT

Methods and devices for removing small negatively charged molecules from a biological sample mixture that uses a solid-phase extraction material that includes a hydrophilic solid support at least partially embedded within a hydrophobic matrix.

64 Claims, 2 Drawing Sheets

U.S. PATENT DOCUMENTS

| | | | |
|---|---|---|---|
| 5,801,237 A * | 9/1998 | Johansson | 536/25.4 |
| 5,834,583 A | 11/1998 | Hancock et al. | |
| 5,856,379 A | 1/1999 | Shiratsuchi et al. | 523/209 |
| 5,869,002 A | 2/1999 | Limon et al. | |
| 5,997,818 A | 12/1999 | Hacker et al. | |
| 6,007,690 A | 12/1999 | Nelson et al. | |
| 6,048,550 A | 4/2000 | Chan et al. | |
| 6,063,838 A | 5/2000 | Patnode et al. | |
| 6,071,406 A | 6/2000 | Tsou | |
| 6,074,827 A | 6/2000 | Nelson et al. | |
| 6,093,558 A | 7/2000 | Seed et al. | |
| 6,103,199 A | 8/2000 | Bjornson et al. | |
| 6,143,247 A * | 11/2000 | Sheppard et al. | 422/63 |
| 6,168,948 B1 | 1/2001 | Anderson et al. | 435/287 |
| 6,197,595 B1 * | 3/2001 | Anderson et al. | 436/180 |
| 6,265,168 B1 * | 7/2001 | Gjerde et al. | 435/6 |
| 6,277,488 B1 | 8/2001 | Kobe et al. | |
| 6,284,113 B1 | 9/2001 | Bjornson et al. | |
| 6,306,273 B1 | 10/2001 | Wainright et al. | |
| 6,319,469 B1 * | 11/2001 | Mian et al. | 422/64 |
| 6,344,326 B1 * | 2/2002 | Nelson et al. | 435/6 |
| 6,383,783 B1 | 5/2002 | Haddad | |
| 6,450,047 B2 * | 9/2002 | Swedberg et al. | 73/863 |
| 6,451,260 B1 * | 9/2002 | Dusterhoft et al. | 422/68.1 |
| 6,504,021 B2 | 1/2003 | Kristyanne et al. | 536/23 |
| 6,617,136 B2 | 9/2003 | Parthasarathy et al. | |
| 6,627,159 B1 | 9/2003 | Bedingham et al. | |
| 6,632,399 B1 * | 10/2003 | Kellogg et al. | 422/72 |
| 6,734,401 B2 | 5/2004 | Bedingham et al. | |
| 6,814,935 B2 | 11/2004 | Harms et al. | |
| 7,026,168 B2 | 4/2006 | Bedingham et al. | |
| 7,192,560 B2 | 3/2007 | Parthasarathy et al. | |
| 2001/0045000 A1 * | 11/2001 | Gundel et al. | 29/458 |
| 2002/0001848 A1 | 1/2002 | Bedingham et al. | |
| 2002/0046966 A1 * | 4/2002 | Muscate-Magnussen | 210/198.2 |
| 2002/0047003 A1 | 4/2002 | Harms et al. | |
| 2002/0048533 A1 | 4/2002 | Harms et al. | |
| 2002/0064885 A1 | 5/2002 | Bedingham et al. | |
| 2002/0182114 A1 * | 12/2002 | Ingenhoven et al. | 422/99 |
| 2003/0013203 A1 * | 1/2003 | Jedrzejewski et al. | 436/102 |
| 2003/0017551 A1 | 1/2003 | Parthasarathy et al. | |
| 2003/0017567 A1 | 1/2003 | Parthasarathy et al. | |
| 2003/0053934 A1 * | 3/2003 | Andersson et al. | 422/72 |
| 2003/0062310 A1 * | 4/2003 | Zare et al. | 210/656 |
| 2003/0138779 A1 | 7/2003 | Parthasarathy et al. | |
| 2003/0228706 A1 | 12/2003 | Ramstad et al. | |
| 2004/0016702 A1 | 1/2004 | Hennessy et al. | |
| 2004/0018116 A1 | 1/2004 | Desmond et al. | |
| 2004/0018559 A1 | 1/2004 | Lau et al. | |
| 2004/0209258 A1 | 10/2004 | Parthasarathy et al. | |
| 2006/0013732 A1 | 1/2006 | Parthasarathy et al. | |

FOREIGN PATENT DOCUMENTS

| | | |
|---|---|---|
| DE | 197 31 670 C2 | 6/2000 |
| EP | 0 309 259 A2 | 3/1989 |
| EP | 0 309 259 A3 | 3/1989 |
| EP | 0 409 432 A2 | 1/1991 |
| EP | 0 409 432 A3 | 1/1991 |
| EP | 0 426 488 A1 | 5/1991 |
| EP | 0 447 362 A1 | 9/1991 |
| EP | 0 309 259 B1 | 6/1994 |
| EP | 0 426 488 B1 | 4/1997 |
| JP | 7-265718 | 10/1995 |
| WO | WO 95/24505 A1 | 9/1995 |
| WO | WO 97/27325 A2 | 7/1997 |
| WO | WO 97/27325 A3 | 7/1997 |
| WO | WO 98/04909 A1 | 2/1998 |
| WO | WO 98/12351 A1 | 3/1998 |
| WO | WO 98/39094 A1 | 9/1998 |
| WO | WO 99/15876 A1 | 4/1999 |
| WO | WO 99/15888 A1 | 4/1999 |
| WO | WO 99/39120 A1 | 8/1999 |
| WO | WO 99/40174 A1 | 8/1999 |
| WO | WO 99/46591 A2 | 9/1999 |
| WO | WO 99/46591 A3 | 9/1999 |
| WO | WO 99/58664 A1 | 11/1999 |
| WO | WO 00/45180 A1 | 8/2000 |
| WO | WO 00/62051 A2 | 10/2000 |
| WO | WO 00/62051 A3 | 10/2000 |
| WO | WO 00/68336 A1 | 11/2000 |
| WO | WO 01/03149 A1 | 1/2001 |
| WO | WO 01/12327 A1 | 2/2001 |
| WO | WO 01/21632 A1 | 3/2001 |
| WO | WO 01/25490 A1 | 4/2001 |
| WO | WO 01/25491 A1 | 4/2001 |
| WO | WO 01/38516 A1 | 5/2001 |
| WO | WO 01/38865 A1 | 5/2001 |
| WO | WO 01/62976 A1 | 8/2001 |
| WO | WO 01/68240 A2 | 9/2001 |
| WO | WO 01/68240 A3 | 9/2001 |
| WO | WO 01/68913 A2 | 9/2001 |
| WO | WO 01/71732 A2 | 9/2001 |
| WO | WO 01/71732 A3 | 9/2001 |
| WO | WO 92/16659 | 10/2002 |
| WO | WO 03/054509 A2 | 7/2003 |
| WO | WO 03/054509 A3 | 7/2003 |
| WO | WO 2004/009851 A2 | 1/2004 |
| WO | WO 2004/010760 A2 | 2/2004 |
| WO | WO 2004/011141 A1 | 2/2004 |
| WO | WO 2004/011142 A1 | 2/2004 |
| WO | WO 2004/011592 A2 | 2/2004 |
| WO | WO 2004/011681 A1 | 2/2004 |

OTHER PUBLICATIONS

American Society of Testing Materials, "ASTM D 570-98, Standard Test Method for Water Absorption of Plastics," *Annual Book of ASTM Standards*, 3 pages (1998).

"AutoSeq96 Dye Terminator Clean-up Kit / Adapter Plate for AutoSeq96," product catalogue [online]. Amersham Biosciences, 2001 [retrieved Dec. 3, 2001]. Retrieved from the Internet: <URL:http://www.apbiotech.com/stiboasp/showmodule.asp?nModuleid=164360>, 2 pages.

"BLAST," National Institutes of Health [online] United States, [retrieved Apr. 19, 2002]. Retrieved from the Internet:<URL:http://www.ncbi.nlm.nih.gov/BLAST/>, 2 pages.

Boom et al., "Rapid and Simple Method for Purification of Nucleic Acids," *Journal of Clinical Microbiology*, Mar. 1990; vol. 28, No. 3; pp. 495-503.

"Porex Corporate Profile," [online]. Porex Corporation, 2001 [retrieved Dec. 5, 2001]. Retrieved from the Internet: <URL:http://www.porex.com/english/corporate/index.asp>, 3 pages.

"Porex Products Group," profile [online]. Porex Corporation, 2001 [retrieved Dec. 5, 2001]. Retrieved from the Internet: <URL:http://www.porex.com/english/porous/index.asp>, 2 pages.

"Purification so fast it'll make your head spin: RapTract Dye Terminator Removal Kit," Prolinx Product Information, Bothell, WA, 2000, 6 pages.

Takeuchi et al., "Ion Chromatography Using Anion Exchangers Modified with Anionic Polysaccharides," LCGC Magazine [online]. LCGC North America, 2001 [retrieved Oct. 2, 2001]. Retrieved from the Internet: <URL:http://www.lcgcmag.com/articles/0004_articles/0004_Takeuchi/0004_Takeuchi.asp>, 12 pages.

"3M Empore Products 96-Well Plates," product listing [online]. 3M Corporation, 1999 [retrieved Dec. 5, 2001]. Retrieved from the Internet: <URL:http://www.mmm.com/empore/formats/Plates/sorbavlb/index.htm>, 2 pages.

"3M Empore Products Empore 96-Well Plates" SPE Extraction Disk Plates & Filter Plates, 3M Extraction Disk Plates for SPE, product listing [online]. 3M Corporation, 1999 [retrieved Dec. 5, 2001]. Retrieved from the Internet: <URL:http://www.mmm.com/empore/formats/Plates/index.htm>, 2 pages.

Tong, et al., "Solid-Phase Method for the Purification of DNA Sequencing Reactions," *Analytical Chemistry*, 1992; vol. 64, No. 22; pp. 2672-2677.

*Hawley's Condensed Chemical Dictionary*, Thirteenth Edition, Revised by Richard J. Lewis, John Wiley & Sons, Inc., Title page, Publication page, and p. 840 (1997). (Exhibit D).

*Stedman's Medical Dictionary*, 27th Edition, Illustrated in Color, Maureen Pugh, Ed., Lippincott Williams & Wilkins, Title page, Publication page, and p. 1072 (2000). (Exhibit E).

"Using Ion Exchange Chromatography to Separate Proteins" datasheet [online]. Access Excellence Activities Exchange @ the National Health Museum, Washington, D.C., 2007 [retrieved on Feb. 28, 2007]. Retrieved from the Internet: <URL:http://cf.acessexcellence.org/AE/AEC/AEF/1994/daugherty_ion.html>; 4 pgs.

U.S. Appl. No. 11/226,161, filed Sep. 14, 2005, Parthasarathy et al.

* cited by examiner

METHODS AND DEVICES FOR REMOVAL OF ORGANIC MOLECULES FROM BIOLOGICAL MIXTURES USING A HYDROPHILIC SOLID SUPPORT IN A HYDROPHOBIC MATRIX

BACKGROUND

Water-soluble dyes (e.g., fluorescent, chemiluminescent, visible, and near-IR) are used routinely in molecular biology to label and monitor components of biological reactions. Frequently, residual dyes as well as other organic molecules should be removed before proceeding with many downstream applications. Thus, the present invention is directed to removing dyes and other organic molecules from biological mixtures, particularly in low volume, microfluidic devices.

There is a significant need for high throughput, low volume, integrated microfluidic devices in order to increase sample throughput and reduce the amount of reagents used per sample (thereby reducing cost per sample) in biological reactions. Small volume Polymerase Chain Reaction (PCR) and nucleic acid cycle sequencing reactions are examples of standard molecular biology techniques that are suitable for incorporation into miniaturized formats. In both applications, removal of residual primers, nucleic acid templates, dyes, and other organic molecules are generally necessary prior to any further downstream applications.

One example where such removal methods are used is in the preparation of a finished sample (e.g., purified nucleic acid materials) from a starting sample (e.g., a raw sample such as blood, bacterial lysate, etc.). For example, to obtain a purified sample of the desired materials in high concentrations, the starting sample is typically prepared for PCR after which the PCR process is performed to obtain a desired common PCR reaction product. The common PCR reaction product can then be used in a variety of molecular biological applications, including, for example, sequencing, cloning, genotyping, and forensic applications.

In fluorescence-based DNA sequencing applications, unincorporated dye terminators (i.e., dye-labeled dideoxy terminators such as dideoxynucleotide triphosphates (ddNTPs)) should preferably be removed from the reaction mixture prior to analysis of the DNA sequence fragments. Failure to sufficiently reduce the concentration of dye terminator molecules leads to dye artifacts (i.e., other dye-containing molecules such as dye-labeled dideoxy terminators such as dideoxynucleotide diphosphates (ddNDPs), dideoxynucleotide monophosphates (ddNMPs), and dideoxynucleosides) that can significantly obscure DNA sequence information. Sequencing reaction purification is a desired step in the preparation of samples prior to sequence analysis, particularly when using a capillary electrophoresis (CE) sequencer.

Conventionally, after completion of the PCR or cycle sequencing reaction, the product is generally purified by either alcohol (ethanol or isopropanol) precipitation or gel filtration chromatography. Other protocols using polyalkylene glycol and biotin-streptavidin interactions have also been utilized for sequencing reaction clean-up. Ultrafiltration membranes, phenol/chloroform extraction, and enzymatic treatments are other methods that are commonly used for purification of PCR and sequencing reaction mixtures.

Such conventional technologies for the purification of PCR and nucleic acid sequencing reactions have not proven to be suitable for incorporation into a microfluidic device. Alcohol precipitation utilizes volatile and flammable reagents. Hydrogels (e.g., crosslinked dextrans), commonly used in size exclusion chromatography, require large bed volumes (10× relative the volume of sample) for efficient separation of impurities from product. Gels are first swollen with a relatively large volume of water, centrifuged, and loaded substantially immediately, because, upon dehydration, these materials are prone to cracking. Biotin-streptavidin mediated purifications require the use of custom biotinylated primers for the efficient capture of product. Biotinylated products are generally captured onto streptavidin-treated paramagnetic particles and physically separated from impurities with the use of a magnet. Alternatively, hybridization based purification (HBP) of the PCR or nucleic acid sequencing product can be accomplished by utilizing primers containing specially designed capture tags. Separation of the nucleic acid fragment from the biological matrix can be achieved by hybridization of the capture tag to a complementary strand bound to a solid support. Both the biotin and HBP strategies would require a rinsing step followed by elution of the sequencing or PCR product from the substrate. Although biotin-streptavidin and HBP purification methods yield clean PCR and sequencing fragments, both approaches require customized primers, which can be cumbersome and expensive.

An alternative approach for the removal of residual dye terminators from DNA sequencing reactions involves treating the reaction mixture with an enzyme (e.g., shrimp alkaline phosphatase) to dephosphorylate residual nucleotide triphosphates. Although cleavage of the phosphate groups(s) from the dye-labeled dideoxynucleotide triphosphates alters the mobility of the dye-labeled nucleotides in the sequencing gel, residual dye moieties are not removed from the reaction mixture by this procedure and must still be eliminated prior to injection of the sample into the sequencer. This is generally accomplished by subsequent alcohol precipitation of the digested product.

PCR and sequencing products can also be effectively purified by adsorption of nucleic acid fragments onto beads and silica gel membranes using chaotropic agents. Impurities (e.g., residual primers, dyes, and salts) can be rinsed from the substrate and the purified product eluted. This multi-step bind/rinse/elute purification scheme may also prove to be cumbersome within the context of a microfluidic device.

Yet another method of removing unwanted materials (e.g., dyes) from cycle sequencing (e.g., Sanger cycling) reaction mixtures involves the use of paramagnetic particles. One example of suitable paramagnetic particles incorporating dye terminator removal materials is available under the trade designation RAPXTRACT from Prolinx Inc., Bothell, Wash. Further examples of these materials (and their methods of use) may be found in U.S. patent application Ser. No. 09/894,810 filed on Jun. 28, 2001 and entitled ENHANCED SAMPLE PROCESSING DEVICES SYSTEMS AND METHODS (U.S. Pat. Application Publication No. 2002/0047003 (Bedingham et al.)). Unfortunately, however, with such particles, the particles must remain in a hydrated state, which limits the ability to prefabricate particle-loaded devices.

Thus, methods are needed for the removal of dyes and other organic molecules from biological mixtures, such as nucleic acid amplification reaction mixtures (e.g., PCR or cycle sequencing reaction mixtures).

SUMMARY OF THE INVENTION

The present invention provides a solid-phase extraction material that includes a hydrophilic solid support (typically in the form of particles) at least partially embedded within a hydrophobic matrix. The present invention also provides methods for processing biological mixtures, i.e., samples containing a biological material such as peptide- and/or nucleotide-containing material, using such solid-phase material. Specifically, the present invention provides methods for the removal of negatively charged organic molecules (e.g., dyes, primers, probes, dNTPs, dye terminators such as ddNTPs, ddNDPs, ddNMPs, and nucleosides) from biological sample mixtures using hydrophilic particles at least partially embedded within a hydrophobic matrix. These methods are based on solid-phase extraction techniques. They are advantageous because they can be incorporated into high throughput, low volume, integrated microfluidic devices, if desired, particularly those being developed for PCR and DNA sequencing.

The present invention provides methods for removing small negatively charged organic molecules (i.e., unwanted molecules) from a biological sample mixture. Preferably, the biological sample mixture is a biological sample mixture such as a nucleic acid amplification reaction mixture (e.g., a PCR reaction mixture or a nucleic acid sequencing reaction mixture).

Herein, "removal" of unwanted molecules involves adhering such molecules to the solid-phase material and allowing desirable products to remain in solution. This is in contrast to conventional elution methods that involve adhering the desirable products to the solid-phase material, washing away the unwanted molecules, and eluting the desirable products to remove them from the solid-phase material.

In one embodiment, a method includes: providing a solid-phase extraction material that includes a hydrophilic solid support (preferably, particles) at least partially embedded within a hydrophobic matrix (preferably, an adhesive); providing a biological sample mixture; and contacting the biological sample mixture with the solid-phase extraction material to remove at least a portion of the small negatively charged organic molecules from the biological sample mixture. Preferably, the hydrophilic solid support is in the form of particles pattern coated on a layer, and at least partially embedded therein, of the hydrophobic matrix (preferably, a silicone, polyvinyl butyral, polyolefin, fluorinated polymer, acrylate, epoxy, natural or synthetic rubber, or combinations (e.g., mixtures, copolymers, terpolymers, etc.) thereof.

In another embodiment, a method includes: providing a device that includes at least one process array that includes a solid-phase extraction material, wherein the solid-phase extraction material includes a hydrophilic solid support (preferably, particles) at least partially embedded within a hydrophobic matrix (preferably, an adhesive); providing a biological sample mixture in the at least one process array; and transferring the biological sample mixture within the at least one process array, wherein the biological sample mixture and the solid-phase extraction material remain in contact for a sufficient time to remove at least a portion of the small negatively charged organic molecules from the biological sample mixture. Preferably, the hydrophilic solid support is in the form of particles pattern coated on a layer of the hydrophobic matrix.

In yet another embodiment, a method includes: providing a device that includes at least one process array that includes a solid-phase extraction material, wherein the solid-phase extraction material includes hydrophilic particles disposed on a layer of a hydrophobic matrix and at least partially embedded therein; providing a biological sample mixture in the at least one process array; and transferring the biological sample mixture within the at least one process array, wherein the biological sample mixture and the solid-phase extraction material remain in contact for a sufficient time to remove at least a portion of the small negatively charged organic molecules from the biological sample mixture. Preferably, the hydrophilic particles are pattern coated on a layer of the hydrophobic matrix.

When the biological sample mixture is a sequencing reaction mixture, the small negatively charged molecules are typically selected from the group consisting of dye-labeled terminators, primers, degraded dye molecules, deoxynucleotide triphosphates, and mixtures thereof. Preferably, for such a sample, the method is carried out under conditions effective to remove substantially all the dye-labeled terminators from the biological sample mixture.

When the biological sample mixture is a PCR reaction mixture, the small negatively charged molecules are typically selected from the group consisting of primers, degraded dye molecules, deoxynucleotide triphosphates, and mixtures thereof. Preferably, for such a sample, the method is carried out under conditions effective to remove substantially all the primers from the biological sample mixture.

The present invention also provides devices that can be used to carry out methods of the present invention. Such devices include analytical receptacles, such as microfluidic devices and microtiter plates, for example.

In one embodiment, the present invention provides a device that includes: a plurality of process arrays that include: a plurality of process chambers, each of the process chambers defining a volume for containing a biological sample mixture; and at least one distribution channel connecting the plurality of process chambers; and a solid-phase extraction material within at least one of the process arrays that includes a hydrophilic solid support (preferably, particles) at least partially embedded within a hydrophobic matrix (preferably, adhesive). Preferably, the device further includes a plurality of valves, wherein at least one of the valves is located along the at least one distribution channel. Preferably, the hydrophilic solid support is in the form of particles pattern coated on a layer of the hydrophobic matrix.

The present invention also provides an analytical receptacle that includes one or more reservoirs and a surface with a cover film adhered to the surface and enclosing the one or more reservoirs. The cover film includes a backing and an adhesive disposed on at least one major surface of the backing and in contact with the receptacle surface. At least a portion of the adhesive has a solid-phase extraction material disposed thereon; wherein the solid-phase extraction material includes hydrophilic particles at least partially embedded in the adhesive.

In another embodiment, the present invention provides an analytical receptacle that includes a plurality of reservoirs adapted for receipt of a biological sample mixture. At least one reservoir includes a solid-phase extraction material that includes hydrophilic particles at least partially embedded in a hydrophobic matrix.

These and other features and advantages of the methods of the invention are described below with respect to illustrative embodiments of the invention.

DETAILED DESCRIPTION OF PREFERRED EMBODIMENTS

The methods of the present invention utilize solid-phase extraction techniques for processing biological sample mixtures to remove at least a portion of small organic molecules (e.g., molecules having a molecular weight of less than about 6,000) included in such mixtures. These small molecules are typically negatively charged and the solid-phase extraction material typically includes a hydrophilic solid support at least partially embedded within a hydrophobic material. The biological sample mixture (i.e., a sample containing a biological material such as peptide- and/or nucleotide-containing material) is preferably a biological reaction mixture (e.g., a PCR or cycle sequencing or other nucleic acid amplification reaction mixture). The small organic molecules are preferably residual or unincorporated materials (including degradation products) in biological reactions (e.g., dyes, primers, probes, dNTPs, dye terminators such as ddNTPs, ddNDPs, ddNMPs, and nucleosides). Significantly, using the solid-phase extraction materials of the present invention, the undesirable molecules preferably preferentially adhere to the solid-phase material and the desirable products remain in the biological sample solution.

Examples of nucleic acid amplification reaction mixtures suitable for use in the present invention include, but are not limited to: a) polymerase chain reaction (PCR); b) target polynucleotide amplification methods such as self-sustained sequence replication (3SR) and strand-displacement amplification (SDA); c) methods based on amplification of a signal attached to the target polynucleotide, such as branched chain DNA amplification; d) methods based on amplification of probe DNA, such as ligase chain reaction (LCR) and QB replicase amplification (QBR); e) transcription-based methods, such as ligation activated transcription (LAT) and nucleic acid sequence-based amplification (NASBA); f) cycle sequencing reactions such as Sanger sequencing; and g) various other amplification methods, such as repair chain reaction (RCR) and cycling probe reaction (CPR).

Such methods are particularly desirable for use in the clean-up of PCR reaction mixtures, nucleic acid sequencing reaction mixtures, nucleic acid labeling reaction mixtures, or hybridization reaction mixtures, particularly PCR, nucleic acid sequencing, and nucleic acid labeling reaction mixtures, and more particularly PCR or nucleic acid cycle sequencing or other amplification reaction mixtures. That is, the methods of the present invention are particularly desirable for removing residual reactants and degradation products thereof (e.g., undesirable dye-containing molecules such as ddNDPs and the like) from the desired amplification reaction products (e.g., PCR or sequencing reaction products). The removal of residual dyes (including near-IR, fluorescent, chemiluminescent, UV, and visible) or dye-containing molecules and other small organic molecules may be important in numerous other genomics and proteomics applications as well (e.g., ligation reactions and protein or peptide affinity binding reactions).

These methods are based on solid-phase extraction techniques, and can be desirably incorporated into high throughput, low volume, integrated microfluidic devices, particularly those being developed for PCR and DNA sequencing. Some desirable qualities of a solid-phase extraction method for PCR or DNA sequencing reaction clean-up for use in an integrated microfluidic device include, for example: 1) the use of high surface area to bed volume ratio porous or nonporous materials that can be incorporated into a spin column, titer well plate, or a well or channel within a flow-through microfluidic device; 2) the use of non-hydrogel based materials that do not require hydration/swelling and are not prone to cracking upon dehydration; 3) no need for specially designed primers or multi-step binding/rinsing/elution protocols; 4) no volatile or corrosive solvents; 5) no leachables that could contaminate DNA products or compromise the structure of the device; and 6) the ability to remove dyes and other residual reactants while not removing a significant amount of PCR or sequencing reaction products.

The methods of the present invention use solid-phase extraction materials effective for selective removal of negatively charged small molecules (e.g., molecules having a molecular weight of less than about 6,000, such as dye terminators), while retaining the larger product molecules (e.g., sequencing ladders), which are often negatively charged as well. Herein, "small organic molecules" refer to molecules in a biological sample mixture, such as a PCR or sequencing reaction mixture or other amplification reaction mixture, that are not the desired product molecules. Typically, the small organic molecules that are removed from biological sample mixtures are smaller than the desired products. Preferably, the small organic molecules that are removed from biological sample mixtures have a molecular weight of less than about 6,000. Such small molecules tend to adhere (i.e., adsorb, absorb, or otherwise bind) to the solid-phase extraction materials of the present invention, whereas molecules with a molecular weight of greater than about 8,000 generally do not. For molecules of intermediate molecular weight, the smaller the molecule, the greater the tendency to adhere (i.e., adsorb, absorb, or otherwise bind), whereas the larger the molecule, the less the tendency to adhere (adsorb, absorb, or otherwise bind). Typically, the desired PCR amplicons have greater than about 50 base pairs and molecular weights of greater than about 33,000. Typically, the desired sequencing ladders have greater than about 18 bases and molecular weights of greater than about 6,000.

The solid-phase extraction materials are typically in the form of particles that include a hydrophilic core as the solid support and a hydrophobic matrix, although this is not a necessary limitation. Suitable hydrophilic solid supports can be porous and nonporous; however, porous materials have the advantage of large surface area to bed volume ratios and are particularly useful in flow-through applications.

Suitable solid supports can be in the form of beads, particles, spheres, films, membranes, frits, foams, microreplicated articles, monoliths, plates, tubes, dipsticks, strips, pads, disks, a ceramic surface deposited on an organic film using, for example, plasma deposition techniques, etc. Solid supports with higher surface areas enhance contact area, which can improve processing efficiency. The solid support can be treated for improved adhesion/surface area by a variety of treatments such as oxygen plasma, diamond-like glass deposition, corona treatment, e-beam or uv radiation, heat, as well as other similar techniques.

Thus, the term "solid support" refers to a porous or nonporous, water-insoluble material. The surface of the solid support can be neutral or charged in nature (preferably, neutral or basic) and is hydrophilic. The solid support can be composed of inorganic particles such as silica, magnesium sulfate, alumina, zirconia, titania, diatomaceous earth, molecular sieves such as zeolites (i.e., sodium and calcium aluminosilicates), hydroxyapatite, iron oxide, and the like; naturally occurring organic polymeric materials, particularly cellulosic materials and materials derived from cellulose, such as fiber-containing papers, e.g., filter paper, chromatographic paper, etc.; synthetic or modified naturally occurring organic polymers, such as nitrocellulose, cellulose acetate, polyacrylamide, crosslinked dextran, amphoteric nylon, and agarose; vitreous materials such as glass, quartz, ceramics, and silicon nitride; or plastics that are intrinsically hydrophilic or have been rendered hydrophilic by the presence of hydrophilic functional groups, such as polyacrylates, polyethylenes, polypropylenes, polystyrenes, polyvinyl chlorides modified with hydrophilic functional groups such as carboxyl, amino, carboxamido, phosphonate, sulfonate, or hydroxyl groups. These materials can be used by themselves or in conjunction with a structural support composed of other materials such as glass, ceramics, metals, plastics, and the like. Other hydrophobic materials (e.g., carbon particles) can be included with the hydrophilic particles as well for various applications.

Preferably, the solid support is in the form of particles. Preferably, the particles have an average particle size (i.e., the largest dimension, typically the diameter) of at least about 5 nanometers (nm), and more preferably, at least about 3 micrometers (i.e., microns or μ or μm). Preferably, the particles have an average particle size of no greater than about 500 microns, and more preferably, no greater than about 100 microns.

The surface area of the particles can vary widely depending on whether the solid support is porous or nonporous. For example, the average surface area can be about 50 square meters per gram ($m^2/g$) to about 200 $m^2/g$.

The hydrophobic matrix includes a material that will absorb less than about 0.5 percent of its weight in water under common hydrophilicity test conditions. A common measure of hydrophobicity of polymers is water absorption by the bulk polymer within 24 hours or at equilibrium as set out in ASTM D570 (standard method to measure water absorption by polymers). There is, however, no commonly agreed definition of hydrophobic and hydrophilic materials. For purposes of this invention, a hydrophobic material is one absorbing less than 0.5 percent of its weight of water within 24 hours, and 4 percent or less at equilibrium. The surface of a solid piece of such a material will typically not wet, and a water drop placed on such an inclined surface will roll off without tailing.

Alternatively, contact angle measurements can be used to determine the hydrophobicity of a material. Hydrophobic materials are those that have a solid-liquid contact angle of greater than about 70°.

Suitable hydrophobic materials include numerous silicones, such as silicone elastomer, room temperature vulcanizable (RTV) silicone rubber, heat vulcanizable silicone rubber, polydimethylsiloxane, poly(vinyl siloxane), silicone-polycarbonate copolymer, polyvinyl butyral, polyolefins (including poly-alpha-olefins), fluorinated polymers such as those disclosed in U.S. Pat. No. 5,380,901 (Antonucci et al.) and perfluorinated (polyether) urethanes, and block copolymers such as those disclosed in U.S. Pat. No. 5,834,583 (Hancock et al.). These may or may not be adhesive formulations.

Other hydrophobic materials include various adhesive compositions including pressure sensitive adhesive and structural adhesives. Such adhesive compositions include acrylates, silicones, natural or synthetic rubbers (e.g., styrene-containing block copolymers), epoxies, and the like. Suitable examples are described in U.S. Pat. No. 4,780,367 (Lau et al.), U.S. Pat. No. 5,183,705 (Birkholz et al.), U.S. Pat. No. 5,294,668 (Babu), U.S. Pat. No. 6,063,838 (Patnode et al.), U.S. Pat. No. 6,277,488 (Kobe et al.), as well as International Publication Nos. WO 00/45180 and WO 00/68336.

The hydrophobic material preferably includes a polymer selected from the group consisting of a silicone, polyvinyl butyral, polyolefin, fluorinated polymer, acrylate, epoxy, natural or synthetic rubber, or combinations (e.g., mixtures, copolymers, terpolymers, etc.) thereof.

Suitable solid-phase extraction materials can be prepared using a variety of techniques. For example, for embodiments in which hydrophilic particles are at least partially embedded within a layer of an adhesive, the hydrophilic particles can be roll coated (or they can be spray coated, dip coated, knife coated, brush coated, or electrostatically deposited, for example) onto a film having a layer of an adhesive thereon. The construction is heated to better anchor the particles and to provide a generally uniform deposition of particles. This processing temperature is dependent on the type of adhesive. Typically, the more particles deposited, the more wettable is the surface, which provides better wicking action, better contact, and often shorter processing times.

Preferably, for embodiments in which hydrophilic particles are at least partially embedded within a layer of an adhesive, the particles are disposed on a layer of adhesive at a coating density of at least about 0.1 milligram (mg) per 12 square millimeters ($mm^2$) surface area, more preferably at a density of least about 0.3 mg/12 $mm^2$ surface area, and most preferably at a density of least about 0.5 mg/12 $mm^2$ surface area. Preferably, the particles are disposed on a layer of adhesive at a coating density of no greater than about 5 mg/12 $mm^2$ surface area, more preferably at a density of no greater than about 1.5 mg/12 $mm^2$ surface area, even more preferably at a density of no greater than about 1.3 mg/12 $mm^2$ surface area, and most preferably at a density of no greater than about 0.9 mg/12 $mm^2$ surface area.

The materials (type of solid support and hydrophobic matrix) and the coating density are selected to provide selective capture of small organic molecules, particularly dye-containing molecules. The solid-phase extraction materials of the present invention provide sites for relatively strong binding of the residual small organic molecules (e.g., dye terminators) while repelling larger negatively charged molecules (e.g., DNA sequencing ladders) based on charge and size effects, thereby allowing for selective clean-up.

The solid-phase extraction materials of the present invention can be used effectively for purification of nucleic acid amplicons after the polymerase chain reaction (PCR), for example. As is well known, PCR allows for analysis of extremely small amounts of nucleic acid (e.g., DNA). Briefly, a nucleic acid molecule (e.g., DNA template) is repeatedly synthesized using a polymerase enzyme (such as Taq DNA polymerase), an excess of two oligonucleotide primers (capable of flanking the region to be amplified and acting as a point of initiation of synthesis when placed under conditions in which synthesis of a primer extension product that is complementary to a target nucleic acid strand is induced), and free deoxynucleotide triphosphates (dNTPs, e.g., dGTP, dATP, dCTP and dTTP), which results in the amplification of a particular sequence by a millionfold or more. The resultant extension or amplification products are typically referred to as "PCR products" or "PCR amplicons."

Preferably, the PCR products incorporate a detectable label or tag, as can other materials in the PCR reaction mixture (e.g., primers and dNTPs). Thus, PCR amplification of target nucleic acid is preferably accomplished by utilizing at least one primer containing a detectable tag. For example, ultraviolet, visible, or infrared absorbing tags could be used that would produce specific ultraviolet, visible, or infrared signals. Examples of a wide variety of tags (a chemical moiety that is used to uniquely identify a nucleic acid of interest) are disclosed in International Publication No. WO 97/27325. Particularly preferred such tags are fluorescent or chemiluminescent agents. These are typically dye compounds that emit visible radiation in passing from a higher to a lower electronic state, typically in which the time interval between adsorption and emission of energy is relatively short, generally on the order of about $10^{-8}$ to about $10^{-3}$ second. Suitable fluorescent or chemiluminescent compounds can include fluorescein, rhodamine, luciferin, as well as a wide variety of others known to one of skill in the art.

In clean-up of PCR reaction mixtures after PCR has occurred, the undesired negatively charged small molecules include residual primers (labeled or unlabeled), degraded dye molecules (i.e., dye molecules or fragments thereof severed from the dye-labeled primers), and dNTPs (labeled or unlabeled). Of these molecules it is particularly important to remove the primers.

Preferably, using the methods of the present invention at least a portion of one or more of these unincorporated materials can be separated from the PCR products (i.e., removed from the PCR reaction mixture). Typically, the smaller molecules are removed (e.g., dNTPs) more easily than the larger molecules (primers). More preferably, at least about 90% of all the residual primers and/or at least about 70% of the dNTPs are removed from a PCR reaction mixture using the methods of the present invention. Even more preferably, substantially all (i.e., at least about 95%) of one or more of the residual primers, degraded dye molecules, and dNTPs, are separated from the desired PCR products. Most preferably, substantially all (i.e., at least about 95%) of all the residual primers, degraded dye molecules, and dNTPs, are separated from the desired PCR products. The level of removal of primers can be determined by the OLIGREEN ssDNA quantitation reagent (Molecular Probes, Eugene, Oreg.), high pressure liquid chromatography (HPLC), and capillary electrophoresis (CE). The level of removal of dNTPs can be determined by absorbance at 1260 nanometers (nm), HPLC, and CE.

Preferably, using the methods of the present invention, at least about 30% of the desired PCR product (e.g., DNA amplicon) is recovered from a PCR reaction mixture. More preferably, at least about 50% of the desired PCR product is recovered from a PCR reaction mixture. Even more preferably, at least about 70% of the desired PCR product is recovered from a PCR reaction mixture. Most preferably, at least about 90% of the desired PCR product is recovered from a PCR reaction mixture. The level of PCR product recovery can be determined by Agilent 2100 Bioanalyzer available from Agilent Technologies, Palo Alto, Calif.

For certain methods of PCR reaction mixture clean-up, the clean-up is preferably carried out at room temperature, although higher temperatures could be used if desired. A typical time for clean-up is less than about 5 minutes.

The solid-phase extraction materials of the present invention can also be used effectively for purification of nucleic acid (e.g., DNA) sequencing ladders after, for example, Sanger cycling. As is well known, sequencing, such as Sanger sequencing, produces a nested set of fragments from a template strand (e.g., a DNA template) by replicating the template strand to be sequenced. Briefly, a nucleic acid molecule (e.g., DNA template) of unknown sequence is combined with a nucleic acid polymerase, a primer, free deoxynucleotide triphosphates (dNTPs, e.g., dGTP, dATP, dCTP and dTTP), and one of the four free dideoxynucleotide triphosphates (a dideoxynucleotide cannot bond to other nucleotides because its 3' end is modified, thus, when dideoxynucleotides are incorporated, strand synthesis stops) to produce a random sample of varying length segments of nucleic acid. Thus, sequencing mixtures contain salts, enzymes, unincorporated deoxynucleotide triphosphates (dNTPs), template nucleic acid, primers, and the resultant nucleic acid sequencing ladders. Various of these materials (e.g., primers and dNTPs) can be labeled with dye molecules or unlabeled. Such mixtures also include unincorporated dye-labeled dideoxynucleotide terminators such as dye-labeled dideoxynucleotide triphosphates (ddNTPs), which can be hydrolyzed (e.g., treated enzymatically with a phosphatase such as shrimp alkaline phosphatase to dephosphorylate residual nucleotide triphosphates) to form dye-labeled artifacts such as dye-labled dideoxynucleotide diphosphates (ddNDPs), dye-labeled dideoxynucleotide monophosphates (ddNMPs), and dye-labeled dideoxynucleosides. As described in International Publication No. WO 01/25490, such unincorporated dye-labeled terminators typically have to be removed from the DNA sequencing ladders prior to electrophoresis. Herein, the "dye-labeled terminators" are also referred to as "dye terminators" and include ddNTPs, ddNDPs, ddNMPs, and dideoxynucleosides. Particularly preferred such dyes are fluorescent or chemiluminescent agents and include fluorescein, rhodamine, luciferin, etc.

In clean-up of sequencing reaction mixtures after cycling has occurred, the undesired negatively charged small molecules include residual primers (labeled or unlabeled), degraded dye molecules (i.e., dye molecules or fragments thereof severed from the dye-labeled terminators), dNTPs (labeled or unlabeled), and dye terminators. Of these, it is particularly important to remove the dye terminators. Preferably, using the methods of the present invention at least a portion of one or more of these unincorporated materials can be separated from the sequencing products (i.e., removed from the sequencing reaction mixture). Typically, the smaller molecules are removed (e.g., dNTPs) more easily than the larger molecules (primers) and the more highly charged molecules are removed more easily than the less highly charged molecules (e.g., the ease of removal decreases from ddNTPs to ddNDPs to ddNMPs to nucleosides). More preferably, substantially all (i.e., at least about 95%) of one or more of the residual primers, degraded dye molecules, dNTPs, and dye terminators are separated from the sequencing products. Most preferably, substantially all (at least about 95%) of all the residual primers, degraded dye molecules, dNTPs, and ddNTPs are separated from the sequencing products. Significantly and preferably, using the methods of the present invention, at least about 95%, more preferably, at least about 98%, and most preferably, 100%, of all the dye terminators are separated from sequencing products. Such products can then be analyzed by sequencing. The level of removal of dye terminators can be determined by fluorescence, CE, or HPLC.

Preferably, using the methods of the present invention, at least about 30% of the desired sequencing product (e.g., DNA ladder) is recovered from a cycle sequencing reaction mixture. More preferably, at least about 50% of the desired sequencing product is recovered from a cycle sequencing reaction mixture. Most preferably, at least about 70% of the desired sequencing product is recovered from a cycle sequencing reaction mixture. The level of product recovery can be determined by CE, for example.

For certain methods of sequencing reaction mixture clean-up, the clean-up is preferably carried out at room temperature, although higher temperatures could be used if desired. A typical time for clean-up is less than about 5 minutes.

The solid-phase extraction materials of the present invention can be incorporated into flow-through devices or non-flow-through formats. If a non-flow-through format is used, the reaction mixture can be incubated with or without mixing, preferably with mixing, for a given period of time and the resultant supernatant containing at least partially purified product (e.g., DNA amplicons) can be removed and analyzed.

Diffusion of small molecules to the solid-phase extraction material can be improved by providing adequate mixing of the reactants. This can be accomplished by vortexing, shaking, heating, sonicating, etc. Providing intimate mixing can result in shorter times for processing (e.g., clean-up), better product recovery levels, and/or better reproducibility.

The solid-phase extraction materials described herein can be incorporated into a variety of devices, particularly analytical receptacles. As used herein, analytical receptacles are devices that receive a sample, reagent, or solvent into one or more reservoirs, which may or may not designed for filtration. Examples include assay plate arrays (e.g., microtiter plates), discrete or continuous (e.g., strip or tape) structures containing a plurality of wells, channels, or other reservoirs, and arrays of the type used in 96-well filter plate assemblies (e.g., of the type described in U.S. Pat. No. 5,620,663 (Aysta et al.)).

Preferred analytical receptacles, without further modification, provide an open system of one or more reservoirs (e.g., wells or channels) to which fluids may be added directly. A cover film is typically applied along the length and width of an analytical receptacle to seal the receptacle, preferably the reservoir(s) of the receptacle, and create a closed system. Preferably, this results in producing individually sealed enclosures, which can be substantially continuous or discrete (i.e., discontinuous) structures.

A cover film, which acts as a sealing membrane, can include an adhesive, preferably, a pressure sensitive adhesive, disposed on a backing (preferably, a transparent backing). The adhesive is selected such that it adheres well to materials of which conventional analytical receptacles are made (preferably polyolefins, polystyrene, polycarbonate, or combinations thereof), maintains adhesion during high and low temperature storage (e.g., about −80° C. to about 200° C.) while providing an effective seal against sample evaporation, and does not substantially dissolve in or otherwise react with the components of the biological sample mixture. Thus, the type of adhesive is not critical as long as it does not interfere (e.g., bind DNA, dissolve, etc.) with the removal of unwanted materials from a biological sample mixture. Preferred adhesives include those typically used on cover films of analytical devices in which biological reactions are carried out. These include poly-alpha olefins and silicones, for example, as described in International Publication Nos. WO 00/45180 and WO 00/68336.

The solid-phase extraction material described herein can be incorporated into the analytical receptacle in a variety of ways. For example, it can be disposed to the walls of one or more reservoirs, it can be in the form of a flow-through membrane placed in one or more reservoirs, it can be disposed to a film (which can be continuous or discontinuous or in the form of a plurality of pieces) placed in one or more reservoirs, or it can be disposed on the cover film.

The solid-phase extraction material described herein is particularly well suited for use in a high throughput microfluidic device resulting in reagent and time savings, as well as elimination of the need to elute in the conventional sense (i.e., washing away the unwanted components from the bound desired products followed by removing the desired products). Such devices typically require low bed volume clean-up media for the purification of small volume reactions. The hydrophilic particles can be incorporated into a microfluidic device in a variety of manners.

In one embodiment, an adhesive-coated cover film of a microfluidic device can be coated with, preferably pattern coated with, the hydrophilic particles. This coating, particularly pattern coating, can be accomplished by a variety of methods such as spray drying, dip coating, brush coating, knife coating, roll coating, ink-jet coating, screen printing, electrostatic deposition, etc. An unpurified biological sample mixture, e.g., a PCR or DNA sequencing reaction mixture, can be spun into a clean-up chamber containing the pattern-coated hydrophilic particles on either or both the top and bottom surfaces of the chamber. The speed of this reaction can be enhanced by intimate contact of the solution with the chamber walls by mixing, vortexing, shaking, or through compression of the walls (made of a compliant material) of the device, etc. The purified reaction mixture is collected and ready for subsequent analysis (e.g., by injection into a DNA sequencing instrument).

In another embodiment, the hydrophilic particles having a hydrophobic matrix coated thereon can be positioned within a microfluidic compartment or channel. For example, a device having at least one process array that includes two connected process chambers, at least one of the process chambers and/or at least one volume defined by a connection (i.e., distribution channel) between at least two process chambers can include the solid-phase material. In this arrangement, if the solid-phase material includes a porous material, an unpurified biological sample solution, e.g., PCR or DNA sequencing reaction mixture, passes through the solid-phase material, allowing sufficient residence time to trap the undesirable components (e.g., excess unincorporated dye terminators). Alternatively, if the solid-phase material includes a nonporous material, the unpurified biological sample solution passes by the material. The contact area of the sample with the solid-phase material can be enhanced upon selection of a solid-phase material within larger surface area. The purified reaction mixture is collected and ready for subsequent analysis, such as occurs, for example, upon injection into a DNA sequencing instrument.

Although the methods of the present invention can be used in a variety of devices, a variety of illustrative embodiments of some suitable devices may be described in, e.g., U.S. patent application Ser. No. 09/894,810 filed on Jun. 28, 2001 and entitled ENHANCED SAMPLE PROCESSING DEVICES SYSTEMS AND METHODS METHODS (U.S. Pat. Application Publication No. 2002/0047003 (Bedingham et al.)) and U.S. patent application Ser. No. 09/895,010 filed on Jun. 28, 2001 and entitled SAMPLE PROCESSING DEVICES METHODS (U.S. Pat. Application Publication No. 2002/0064885 (Bedingham et al.)). Other useable device constructions may be found in, e.g., U.S. Provisional Patent Application Ser. No. 60/214,508 filed on Jun. 28, 2000 and entitled THERMAL PROCESSING DEVICES AND METHODS; U.S. Provisional Patent Application Ser. No. 60/214,642 filed on Jun. 28, 2000 and entitled SAMPLE PROCESSING DEVICES, SYSTEMS AND METHODS; U.S. Provisional Patent Application Ser. No. 60/237,072 filed on Oct. 2, 2000 and entitled SAMPLE PROCESSING DEVICES, SYSTEMS AND METHODS; U.S. Provisional Patent Application Ser. No. 60/260,063 filed on Jan. 6, 2001 and titled SAMPLE PROCESSING DEVICES, SYSTEMS AND METHODS; U.S. Provisional Patent Application Ser.

No. 60/284,637 filed on Apr. 18, 2001 and titled ENHANCED SAMPLE PROCESSING DEVICES, SYSTEMS AND METHODS; and U.S. patent application Ser. No. 09/895,001 filed Jun. 28, 2001 and entitled SAMPLE PROCESSING DEVICES AND CARRIERS METHODS (U.S. Pat. Application Publication No. 2002/0048533 (Harms et al.)).

The methods described herein can be used in a variety of different processes requiring at least partial removal of dyes or other organic molecules from biological reaction mixtures contained in the process arrays of microfluidic devices. Examples of such processes involve the clean-up of chemical reaction mixtures, e.g., nucleic acid amplification, which may or may not also be carried out in process arrays of the device. Some or all of the required reagents for clean-up may be present in the device as manufactured, they may be loaded into the process arrays after manufacture of the device, they may be loaded in the process arrays just before introduction of the sample, or they may be mixed with sample before loading into the process arrays.

A preferred method involves the use of a device with a plurality of process arrays such as those illustrated in U.S. patent application Ser. No. 09/894,810 filed on Jun. 28, 2001 and entitled ENHANCED SAMPLE PROCESSING DEVICES SYSTEMS AND METHODS METHODS U.S. Pat. Application Publication No. 2002/0047003 Bedingham et al.)). Each of the process arrays includes a number of chambers (e.g., loading chambers and process chambers such as reaction chambers or clean-up chambers) that are preferably arranged generally radially on a device (such that centrifugal forces can move fluids sequentially from chamber to chamber, for example). The chambers within each of the arrays are in fluid communication using channels or other conduits that may, in some embodiments, include valve structures to control the movement as desired.

Using such a device, starting sample material, e.g., lysed blood cells, is provided in a loading chamber. A filter is preferably provided to filter the starting sample material as it moves from the loading chamber to a first process chambers. The first process chambers preferably include suitable PCR primers as supplied, e.g., dried down in each of the chambers. Each of the chambers may include the same primer or different primers depending on the nature of the investigation being performed on the starting sample material. One alternative to providing the primers in the process chambers before loading the sample is to add a suitable primer to the loading chamber with the starting sample material (provided that the primer is capable of passing through the filter, if present).

After locating the starting sample material and any required primers in the process chambers, the materials in the process chambers are thermally cycled under conditions suitable for PCR amplification of the selected genetic material.

After completion of the PCR amplification process, the materials in each of the first process chambers may be moved through another filter chamber (one filter chamber for each process chamber) to remove unwanted materials from the amplified materials, e.g., PCR primers, unwanted materials in the starting sample that were not removed by filter, etc. The filter chambers contain the solid-phase extraction materials (e.g., hydrophilic particles) described above for sample clean-up (e.g., dye removal). The area in which the solid-phase extraction material is included in such devices can be a chamber or in the volume defined by a connection between two chambers or both.

After clean-up of the sample materials in the filter chambers, the filtered PCR amplification products from each of the first process chambers are moved into second process chambers for, e.g., sequence cycling of the genetic materials amplified in the first process chambers through appropriate control of the thermal conditions encountered in second process chambers.

After completion of the sequence cycling (e.g., Sanger sequencing) process, the materials in each of the second process chambers may be moved through another filter chamber (one filter chamber for each process chamber) to remove unwanted materials from the sequencing ladders (e.g., sequencing primers, ddNTPs, etc.). The filter chambers contain the solid-phase extraction materials (e.g., hydrophilic particles with hydrophobic matrix) described above for sample clean-up (e.g., dye removal). Again, the solid-phase extraction material can be in a chamber or between chambers in a channel.

The present invention also provides devices for processing (e.g., clean-up) of sample mixtures. The sample materials may be located in a plurality of chambers in the device which, in various aspects, may include one or more of: a reflective layer (e.g., a metallic layer); baffle structures to enhance cooling during rotation of the device; capture plugs to capture filtering materials; valve mechanisms capable of being selectively opened, thermal indicators for monitoring/controlling the temperatures in process chambers, absorptive materials in the process chambers to enhance energy absorption, etc. In various embodiments, the devices may include reagents, filters, and other sample processing materials in the process chambers.

Among the thermal control advantages of the devices of the present invention are chamber-to-chamber temperature uniformity, comparable chamber-to-chamber temperature transition rates, and the increased speed at which thermal energy can be added or removed from the process chambers. Among the device features than can contribute to these thermal control advantages are the inclusion of a reflective layer (e.g., metallic) in the device, baffle structures to assist in removing thermal energy from the device, and low thermal mass of the device. By including thermal indicators in the devices, enhanced control over chamber temperature may be achieved even as the device is rotated during processing.

Figure 1:
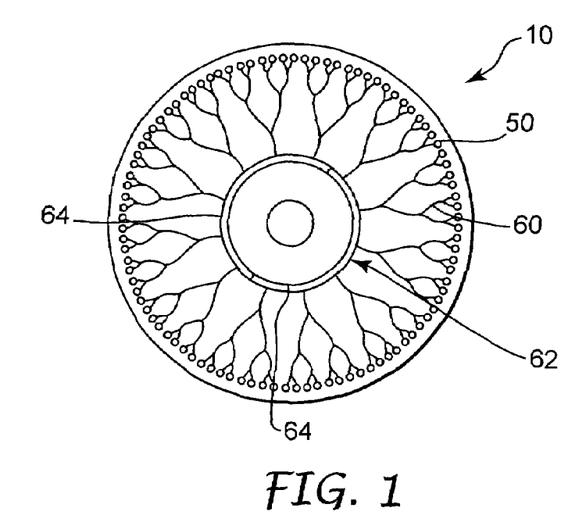
FIG. 1 is a top plan view of one device that can be used in connection with the present invention.

One illustrative device manufactured according to the principles of the present invention is illustrated in FIG. 1. The device 10 is preferably in the shape of a circular disk as illustrated in FIG. 1, although any other shape that can be rotated could be used in place of the preferred circular disc. The device 10 of FIG. 1 is a multi-layered composite structure including a substrate, first layer, and a second layer.

The device includes a plurality of process chambers 50, each of which defines a volume for containing a sample and any other materials that are to be thermally cycled with the sample. The illustrated device 10 includes ninety-six process chambers 50, although it will be understood that the exact number of process chambers provided in connection with a device manufactured according to the present invention may be greater than or less than ninety-six, as desired.

The process chambers 50 in the illustrative device 10 are in the form of wells, although the process chambers in devices of the present invention may be provided in the form of capillaries, passageways, channels, grooves, or any other suitably defined volume. The process chambers 50 are in fluid communication with distribution channels 60 that, together with the common loading chamber 62, provide a distribution system for distributing samples to the process chambers 50. Introduction of samples into the device 10 through the loading chamber 62 may be accomplished by rotating the device 10 about a central axis of rotation such that the sample materials are moved outwardly due to centrifugal forces generated during rotation. Before the device 10 is rotated, the sample can be introduced into the loading chamber 62 for delivery to the process chambers 50 through distribution channels 60. The process chambers 50 and/or distribution channels 60 may include ports through which air can escape and/or features to assist in distribution of the sample materials to the process chambers 50. Alternatively, it may be possible to provide a closed distribution system, i.e., a system in which materials may be introduced through an opening through which air within the process chambers 50 and/or distribution channels 60 also escapes during the distribution process. In another alternative, sample materials could be loaded into the process chambers 50 under the assistance of vacuum or pressure.

The process chamber 50, associated distribution channels 60, and loading chamber 62 all combine to form a number of process arrays on the device 10, with each process array including one of the process chambers 50, the distribution channels 60 connecting the process chamber 50 to the loading chamber 62, and the loading chamber 62 itself. The process arrays may preferably be arranged radially on the device 10.

Figure 2:
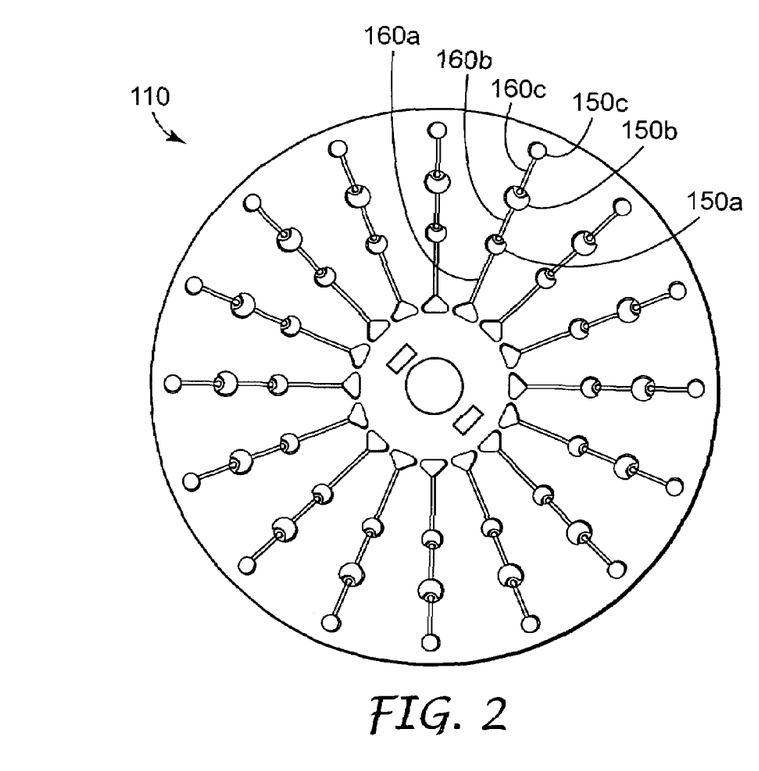
FIG. 2 depicts an alternative device that can be used in connection with the present invention.
Figure 3:
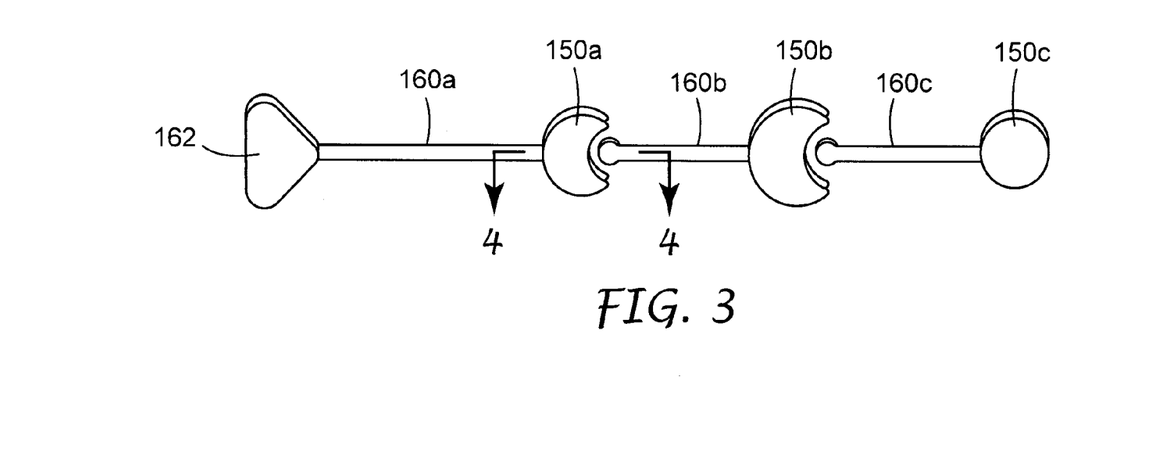
FIG. 3 is an enlarged view of one process array on the device of FIG. 2.
Figure 4:
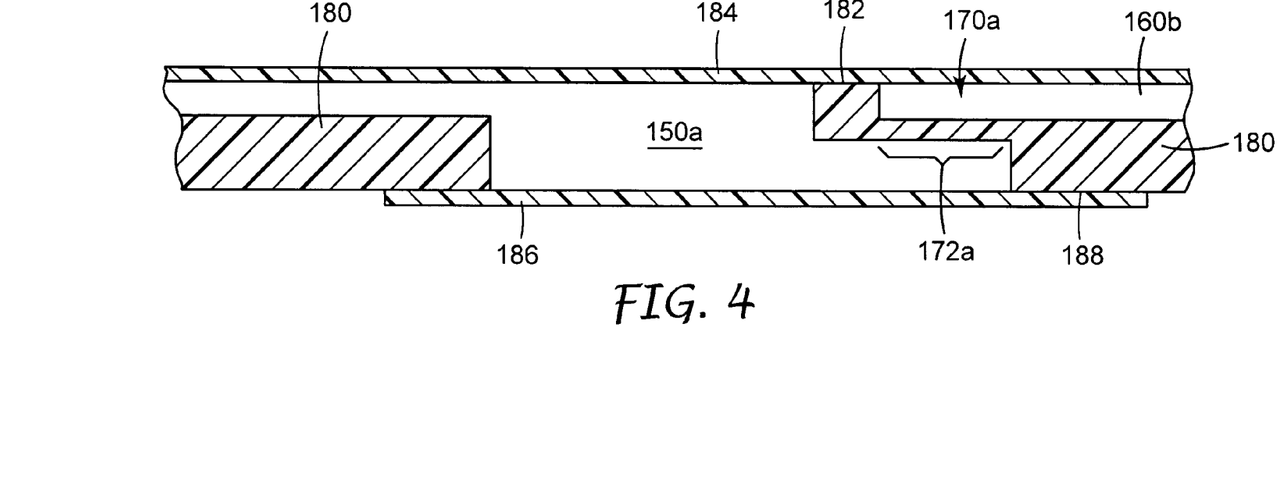
FIG. 4 is a cross-sectional view of a portion of the process array of FIG. 3, taken along line 4-4 in FIG. 3.

Referring to FIGS. 2-4, an alternative device 110 with a different arrangement of process arrays is depicted that can be used in place of the device 10 of FIG. 1. The device 110 seen in FIG. 2 includes a number of independent process arrays, each of which includes distribution channels 160*a* and 160*b* connecting a loading chamber 162 and process chambers 150*a*, 150*b* and 150*c*. The process arrays on the device 110 are independent in the sense that the different process arrays are not in fluid communication with each other as are the process arrays on the device 10 of FIG. 1, but are, instead, separate and distinct from each other.

It is preferred that the process arrays be arranged radially from the center of the device 110. As a result, rotation of the device can be used to move sample materials successively through the chambers and distribution channels. The depicted device 110 includes sixteen process arrays, although it will be understood that devices used in connection with the present invention can include any desired number of process arrays. Furthermore, although each of the process arrays of device 110 includes a loading chamber and three process chambers connected sequentially by distribution channels, it should be understood that a process array of the present invention may include as few as two interconnected chambers.

FIG. 3 is an enlarged view of one process array on device 110 and FIG. 4 is a cross-sectional view of a portion of the process array of FIG. 3. Each process array includes a loading chamber 162 connected to a first process chamber 150*a* through a distribution channel 160*a*. The first process chamber 150*a* is, in turn, connected to a second process chamber 150*b* through a distribution channel 160*b*. The second process chamber 150*b* is connected to a third process chamber 150*c*, that, in the depicted process array, is located furthest from the loading chamber 162. If materials are to be moved within the process array from the loading chamber 162 towards the third process chamber 150*c*, it may be preferred that the loading chamber 162 be located closer to the axis of rotation of the device than the process chambers 150*a*, 150*b* or 150*c*.

The cross-sectional view of FIG. 4 depicts a number of other features of one potential construction of a device that could be used in connection with the present invention. The construction includes a core 180 in which the features of the device are formed. One surface 182 of the core 180 may include a cover film 184 attached thereto. The cover film 184 may be of any suitable construction, although the adhesive cover films described herein may be preferred.

The bottom of the process chamber 150*a* also includes a cover 186 attached to the surface 188 of the core 180 to enclose the volume of the process chamber 150*a*. Like the cover 184, it may be preferred that the cover 186 be attached to and seal with the core 180 using an adhesive, e.g. a pressure sensitive adhesive as described herein. It may be preferred that the cover 186 be provided in the form of a metallic layer that enhances thermal energy transfer into and out of the process chamber 150*a*. In some embodiments, the cover 186 may be provided in the form of a ring-shaped structure as described in, e.g., U.S. patent application Ser. No. 09/894,810 filed on Jun. 28, 2001 and entitled ENHANCED SAMPLE PROCESSING DEVICES, SYSTEMS AND METHODS METHODS (U.S. Pat. Application Publication No. 2002/0047003 (Bedingham et al.)).

The first process chamber 150*a* includes a valve structure in the form of a lip 170*a* that protrudes into the boundaries of what would otherwise be a generally circular first process chamber 150*a*. The lip 170*a* is in the form of an undercut extension into the volume of the process chamber 150*a* as seen in, e.g., FIG. 4. When an opening is provided in the lip 170*a*, sample materials in the process chamber 150*a* can move into the distribution channel 160*b* for delivery to the second process chamber 150*b* is desired. In the absence of an opening in the lip 170*a*, movement of materials into the second process chamber 150*b* through distribution channel 160*b* is prevented by the lip 170*a* which otherwise seals against the cover 184 to prevent the flow of sample materials from the first process chamber 150*a* into the distribution channel 160*b*.

The lip 170*a* may preferably include an area 172*a* of reduced thickness. This may be seen best in the cross-sectional view of FIG. 4. When the area 172*a* is, e.g., pierced or otherwise deformed to include an opening formed therethrough, any sample materials located in the volume of the process chamber 150*a* can move from the chamber into the distribution channel 160*b* for delivery to the second process chamber 150*b*.

Although it is not required, the reduced thickness of the area 172*a* may provide a number of advantages. It may, for example, limit the location or locations in which the lip 170*a* may be easily pierced to provide the desired opening, i.e., the thicker portions of the lip 170*a* surrounding the area 172*a* may be more resistant to piercing by any of the techniques that could be used to pierce the lip 170*a* to form an opening therethrough. The techniques that could be used to pierce the lip 170*a* may include, e.g., mechanical piercing (using, e.g., a pin, needle, etc.), laser ablation, etc. Another potential advantage of the area 172*a* of reduced thickness is that it can be molded into the core layer 180 along with, e.g., the process chambers and distribution channels.

Although devices such as those described herein may be well-suited to performing processes such as e.g., PCR, Sanger sequencing, etc., devices of the invention may be limited to clean-up of the products of such processes which may be performed off of the devices.

Rotation of any device including process arrays such as those depicted in FIGS. 1-4 may be used to facilitate mixing through mechanical agitation of the sample materials and any other materials (e.g., reagents, etc.) present in the process chambers. The mechanical agitation may be accomplished by oscillating the device in opposite directions about the axis of rotation. The oscillations may vary in frequency and/or magnitude depending on a variety of factors, e.g., the size/shape of the process chambers, the amount of materials in the process chambers, viscosities, temperatures, stability of the sample materials, etc. For example, it may be useful to accomplish mixing by oscillating the device 10 at a frequency of about 1 Hertz (Hz) to about 100 Hertz. The magnitude of the oscillations may be, e.g., from about 5 degrees to about 360 degrees.

The mechanical agitation can be carried out during, for example, PCR, Sanger cycling, clean-up of the PCR reaction mixture, clean-up of the sequencing reaction mixture, as well as during various other processes that can be carried out in the microfluidic devices described herein. Similarly, mechanical agitation by rotation, or other means, can be carried out on any of the devices described herein.

EXAMPLES

Objects and advantages of this invention are further illustrated by the following examples, but the particular materials and amounts thereof recited in these examples, as well as other conditions and details, should not be construed to unduly limit this invention.

Example 1

Preparation of Alumina/Adhesive Composite

A tape with a hydrophobic adhesive was immersed face down in a bed of ceramic particles. The alumina particles ranged in size from 3 micrometers (micron or μ or μm) to 6μ (ICN, Costa Mesa, Calif.). Pressure was applied to the top surface to achieve maximum efficiency of particle packing. This assembly was placed in an oven for 30 minutes at temperatures ranging from 40° C. to about 120° C. depending on the adhesive. The assembly was then allowed to cool to room temperature in a chemical hood. Excess particles were removed using air. The alumina/adhesive composite was then used for clean-up of unpurified sequencing reaction.

The adhesive tapes used were SCOTCH Brand 143 Mailing Tape, Stock Number 34-8501-9760-6, 3M, St. Paul, Minn. 55144; SCOTCH Brand 3561-C Packaging Tape, Stock Number 34-8506-0549-3, St. Paul, Minn. 55144; SCOTCH Brand 2020 Masking Tape, Stock Number CV-0001-8259-8, St. Paul, Minn. 55144; and TIMEMED Brand TSI-501 Autoclave Tape, Fisher Catalog Number 11-875-52, Pittsburgh, Pa.

A goniometer (model 100-00 115; Ramé-Hart, Inc., Mountain Lakes, N.J.) was used to measure the contact angle between the alumina/adhesive composite (solid surface) and a sessile drop of water (liquid) at ambient temperatures. The alumina/adhesive composite was laid flat upon a stage and a cross beam of light was passed through a 5 microliters (μL) water drop placed on the surface of the material. The solid-liquid (SL) angle was determined and the values were used to gauge surface property changes of the adhesive before and after embedding of alumina particles into the adhesive. Generally, adhesives have a high SL contact angle of greater than 90°. After introduction of alumina particles onto the adhesive and heating, the contact angle of water dropped significantly, typically to between 10° and 40°, making the surface highly wettable. The heat processing helped to embed the particles into the adhesive matrix and provide a uniform surface that resulted in reproducible performance of the composite material for clean-up of amplification reactions. Scanning electron microscope (SEM) micrographs were used to investigate the topography of the alumina/adhesive composite. Micrographs were taken at 1000×, 2000×, and 3000× on a series of alumina particles embedded into various adhesives. Typical scanning electron micrographs indicated that the particles were uniformly distributed on the tape.

Example 2

Preparation of a Microfluidic Disk and Sequencing Reaction Clean-up

A simplified microfluidic disk was used that consisted of eight duplicate processing lanes arranged radially in a laminated polypropylene disk (80 millimeter (mm) diameter, 0.030 inch thick (762 μm thick). Each processing lane consisted of a single combined input and clean-up chamber (circular well, 7.11 mm diameter, located on a 16.5 mm radius) that was connected to an output chamber (circular well, 4 mm diameter, located on a 29.0 mm radius) by a single channel (0.010 inch deep (254 μm deep), 0.015 inch wide (381 μm wide)).

A 4-mm disk (12 mm$^2$ surface area) was punched from the alumina/adhesive composite and adhered onto the clean up chamber of the microfluidic disc. These 4-mm discs were positioned onto an adhesive cover film (9795R Advanced Sealing Tape, 3M Medical Specialties, St. Paul, Minn.) which was laminated onto a microfluidic disk with the 4-mm disk registered such that it covered the top and/or bottom clean-up chambers. Ten microliters (10 μL) quarter strength BIGDYE Terminators v 2.0 (Applied Biosystems, Inc., Foster City, Calif.) cycle sequencing reaction mixtures containing 2 μL BIGDYE mix, 200 nanograms (ng) DNA template, and 1.6 picomoles of a primer were thermocycled according to manufacturers instructions in a GENEAMP PCR System 9700 thermocycler (Applied Biosystems Inc.). Five microliters (5 μL) of unpurified sequencing reaction were introduced into the clean-up chamber and allowed to contact the particles by shaking the disk at a frequency of 12-14 Hz with an angular displacement of 20 degrees for 2 to 5 minutes to achieve active mixing of the solution with the ceramic surface. During this time, the smaller molecules in the unpurified sequencing reaction mixture (containing dye terminators and their hydrolysis products, DNA template, Taq polymerase, buffer, dNTPs, and primer) were bound to the alumina/adhesive composite and the DNA ladder was left in solution. Removal of the solution from the clean-up chamber followed by dilution to 10 to 20 μL in sterile water yielded a sample that was ready for further analysis as described below in Examples 3 and 4.

Example 3

Screening of Alumina/Adhesive Composite for Clean-up of BIGDYE Terminators v 2.0 Using Capillary Electrophoresis and Reverse Phase HPLC.

Capillary electrophoresis(CE) and reverse phase high pressure liquid chromatography (HPLC) were used as analytical tools to evaluate the performance of materials for clean-up of sequencing reactions, specifically removal of dye terminators and sequencing ladder recovery, prior to sequencing analysis by ABI PRISM 3100 Genetic Analyzer (Applied Biosystems, Inc.).

Capillary Electrophoresis (CE). Capillary electrophoresis analyses of purified sequencing reactions were done with Beckman P/ACE MDQ Capillary Electrophoresis instrument (Beckman Coulter, Fullerton, Calif.) with a fluorescence detector (488 nm excitation, 530 to 700 nm emission) using a 75 micrometer ID, 30 cm long (20 cm to the detector) fused silica capillary. Runs were performed at 500 volts per centimeter (V/cm) (15 KV total) using 50 nanomolar (mM) Tris-HCl/1 mM EDTA (pH 8.5) as the running buffer. Sample injection was done at 690 pascals for 5 seconds. The conditions used gave good separation of the dye terminators (all the four ddNTPs corresponding to the four bases, A, T, G, C as one peak with a retention time of 3.2 minutes) and its degradation products (as one peak with a retention time of 2.2 minutes) and the combined sequencing ladder (as one peak with a retention time of 4.1 minutes). Sequencing ladder and dye terminator concentrations were obtained by integrating the peak area of the various analytes. For each of the samples, the baseline was subtracted from the analyte values and the resulting analyte concentration was represented as a percentage of the starting sequencing reaction. The data revealed that the dye terminator removal and sequencing ladder recovery was dependent on time of contact of the solution with the alumina/adhesive composite and uniform distribution of particles onto the surface, but not significantly on the type of adhesive or particle density. For particularly good sequencing data, the samples fulfilled the following two conditions: 1) dye terminator removal was greater than 98%; and 2) recovery of sequencing ladder was at least 30%.

Reverse Phase HPLC. HPLC analysis of purified sequencing reactions was performed on a Waters ALLIANCE 2690 (Waters Corporation, Milford, Mass.) separations module with a Waters 474 Scanning Fluorescence detector and Waters 996 Photodiode array detector and a C18 column. The mobile phase used was 70% triethylamine acetate (TEAaC) and 30% acetonitrile with a flow rate of 0.1 milliliter per minute (mL/min). A 2.5-µL sample of purified sequencing reaction was injected and the run time was for 15 minutes. Analysis was done using the fluorescence detector and the conditions used gave good separation of the dye terminators (all the four ddNTPs corresponding to the four bases, A, T, G, C as one peak) and their degradation products (as one peak). The dye terminator concentrations were obtained by integrating the peak area of the various analytes. For each of the samples, the baseline was subtracted from the analyte values and the resulting analyte concentration was represented as a percentage of the starting sequencing reaction. Again, the data revealed that the dye terminator removal and sequencing ladder recovery was dependent on time of contact of the solution with the alumina/adhesive composite and uniform distribution of particles onto the surface, but not significantly on the type of adhesive or particle density and to obtain good sequencing data. For particularly good sequencing data, the dye terminator removal was greater than 98%. These results correlated well with the results obtained using capillary electrophoresis.

Example 4

BIGDYE Terminators v 2.0 Sequencing Reaction Clean-up Using 3-6µ Aumina Particle/Adhesive Composite An alumina/adhesive composite using 3-6µ particles (ICN) was prepared as described in Example 1 on various adhesive tapes. Five microliters (5 µL) of unpurified BIG-DYE Terminators v 2.0 quarter strength sequencing reaction was cleaned up using a microfluidic disk containing the alumina/adhesive composite in the clean-up chambers as described in Example 2. The purified sequencing reaction samples were analyzed under standard sequencing conditions using an ABI PRISM 3100 Genetic Analyzer (Applied Biosystems, Inc.). The resulting electropherograms were manually checked for quality (like dye blobs, number of Ns) and compared against the reference sequence using the BLAST program available through GenBank.

In addition, the electropherograms were analyzed using Phred base calling program (Codoncode Corp., Dedham, Mass.). The Phred program generates highly accurate, base-specific quality scores and the quality scores are an ideal tool to assess the quality of sequences. The Phred quality scores generated for sequencing reactions purified using alumina/adhesive composites on different adhesive tapes are shown below in Table 1. The results indicated that the alumina/adhesive composites gave good sequence data and was comparable to data generated using CENTRISEP columns (Princeton Separations, Adelphia, N.J.) which is considered an industry standard. Average read length of successful reactions was 500 bases with 97% to 98% base-calling accuracy.

TABLE 1

| Sample | Scores ≧ 20 | Scores ≧ 30 | Scores ≧ 40 | Classification |
|---|---|---|---|---|
| 3-6µ SCOTCH Brand 143 Mailing Tape | 488 | 380 | 266 | Good |
| 3-6µ TIMEMED Brand TSI-501 Autoclave Tape | 462 | 339 | 275 | Good |
| 3-6µ SCOTCH Brand 2020 Masking Tape | 365 | 237 | 163 | Good |
| 3-6µ SCOTCH Brand 3561-C Packaging Tape | 504 | 395 | 276 | Good |
| CENTRISEP | 610 | 418 | 291 | Good |

Example 5

BIGDYE Terminators v 2.0 Sequencing Reaction Clean-up Using Scotch Brand 143 Mailing Tape with Various Size Alumina Particle/Adhesive Composite Alumina/adhesive composites using particles ranging in size from 3 to 6µ to 32 to 63µ (ICN) and 20 to 100µ (Sigma Aldrich, St. Louis, Mo.) were prepared on the SCOTCH brand 143 Mailing Tape as described in Example 1. Five microliters (5 µL) of unpurified BIGDYE Terminators v 2.0 quarter strength sequencing reaction was cleaned up using a microfluidic disk containing the alumina/adhesive composites in the clean-up chambers as described in Example 2. The purified sequencing reaction samples were analyzed under standard sequencing conditions using an ABI PRISM 3100

Genetic Analyzer, Applied Biosystems, Inc. The resulting electropherograms were manually checked for quality and base calling accuracy using BLAST and Phred program as described in Example 4. The Phred quality scores generated for sequencing reactions purified using different size alumina particle/adhesive composite on mailing tape are shown below in Table 2. The results indicated that the alumina/adhesive composites gave good sequence data and was comparable to data generated using CENTRISEP columns. Average read length of successful reactions was 500 to 600 bases with 97% to 98% base-calling accuracy.

TABLE 2

| Sample | Scores ≧ 20 | Scores ≧ 30 | Scores ≧ 40 | Classification |
| --- | --- | --- | --- | --- |
| 3-6µ | 511 | 400 | 294 | Good |
| 7-12µ | 534 | 416 | 297 | Good |
| 10-18µ | 508 | 389 | 294 | Good |
| 18-32µ | 530 | 396 | 301 | Good |
| 32-63µ | 505 | 368 | 244 | Good |
| 50-200µ neutral | 494 | 350 | 233 | Good |
| 100µ neutral | 500 | 359 | 228 | Good |
| 100µ acidic | 426 | 328 | 271 | Good |
| 100µ basic | 549 | 412 | 338 | Good |
| CENTRISEP | 638 | 436 | 330 | Good |

Example 6

Polymerase Chain Reaction (PCR) Clean-up Using Alumina/Adhesive Composite

Briefly, a typical PCR reaction contains 200 nM of each of the two primers and 200 µM of each of the four dNTPs (dGTP, dATP, dCTP, and dTTP). Most of the residual primers and dNTPs after a thermocycling reaction need to be removed as the residual dNTPs and primers can interfere in subsequent down-stream applications such as sequencing reaction. At the same time sufficient amount of PCR product needs to be recovered for further processing. The ability of alumina/adhesive composites to remove primers and dNTPs and recover PCR amplicons and clean-up a PCR reaction for further processing was analyzed.

Primer removal: A known amount (1 to 10 picomoles) of an oligonucleotide (M13/PUC sequencing primer (−47) (24-mer), New England Biolabs, Beverly, Mass.) in 5 µL of water (distilled, deionized, and autoclaved) was added to a 32-63µ alumina particles coated on the SCOTCH Brand 3561-C Packaging Tape (occupying a space of 4 mm diameter) adhered to the clean-up chamber of the microfluidic disk as described in Example 2. The solution was allowed to contact the particles by shaking the disk at a frequency of 12-14 Hz with an angular displacement of 20 degrees for 2 to 5 minutes to achieve active mixing of the solution with the alumina/adhesive composite surface and the clean solution was removed from the clean-up chambers for further analysis. The amount of primers remaining in the solution was determined using the OLIGREEN ssDNA quantitation reagent (Molecular Probes, Eugene, Oreg.). This material was very effective in removing about 80% of the primers even at a concentration of 10 picomoles within 5 minutes of incubation.

dNTP removal: A known amount of dNTPs (8 nanomoles with equal amounts of each of the four dNTPs) in 5 µL of water (distilled, deionized, and autoclaved) was added to a 32-63µ alumina particles coated on the SCOTCH brand 3561-C Packaging Tape (occupying a space of 4 mm diameter) adhered to the clean-up chamber of the microfluidic disk as described in Example 2. The solution was allowed to contact the particles by shaking the disk at a frequency of 12-14 Hz with an angular displacement of 20 degrees for 2 to 5 minutes to achieve active mixing of the solution with the alumina/adhesive composite surface and the clean solution was removed from the clean-up chambers for further analysis. The amount of dNTPs remaining in the solution was determined using absorbance at 260 nm in a spectrophotometer. Again, this material was effective in removing about 80% of the dNTPs within 5 minutes of shaking.

PCR product purification and recovery in a microfluidic disk: A known amount of PCR amplicon (10 to 17 ng) ranging in size from 150 to 930 base pairs (bp) in 5 µL of water (distilled, deionized, and autoclaved) was added to a 32-63µ alumina particles/adhesive composite on the SCOTCH Brand 3561-C Packaging Tape (occupying a space of 4 mm diameter) adhered to the clean-up chamber of a microfluidic disk as described in Example 2. The solution was allowed to contact the particles by shaking the disk at a frequency of 12-14 Hz with an angular displacement of 20 degrees for 2 to 5 minutes to achieve active mixing of the solution with the alumina/adhesive composite surface and the clean solution was removed from the clean-up chambers for further analysis. The amount of PCR amplicon remaining in the supernatant was determined by Agilent 2100 Bioanalyzer using a DNA 7500 lab chip kit (Agilent Technologies). The 32-63µ alumina particles/adhesive composite gave good recovery, a minimum of 90%, independent of the size of the PCR amplicon. The purified PCR amplicons were used for sequencing and the sequencing reactions were purified with 3-6µ alumina particle/adhesive composite on SCOTCH Brand 143 Mailing Tape and analyzed by ABI PRISM 3100 Genetic Analyzer under standard sequencing conditions (Applied Biosystems, Inc.). The resulting electropherograms were evaluated as described in Example 4. The electropherograms gave good sequencing data and yielded Phred scores of ≧20 for 500 to 600 bases (for larger amplicons).

Patents, patent applications, and publications disclosed herein are hereby incorporated by reference (in their entirety) as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. A method of removing small negatively charged organic molecules from a biological sample mixture, the method comprising:
providing a device comprising a plurality of process arrays, wherein each process array of the plurality of process arrays comprises:
a plurality of process chambers, each of the process chambers defining a volume for containing a biological sample mixture; and
at least one distribution channel connecting the plurality of process chambers of the array; wherein at least one of the process arrays comprises, within the array, a solid-phase extraction material comprising solid hydrophilic particles of a hydrophilic solid support partially embedded within a hydrophobic matrix, and further wherein the solid hydrophilic particles comprise molecules different than the hydrophobic matrix;

providing a biological sample mixture; and contacting the biological sample mixture with the solid-phase extraction material to remove at least a portion of the small negatively charged organic molecules from the biological sample mixture.

2. The method of claim 1 wherein the particles have an average particle size of at least about 5 nm.

3. The method of claim 2 wherein the particles have an average particle size of no greater than about 500 microns.

4. The method of claim 1 wherein the particles of hydrophilic solid support comprise a material selected from the group consisting of inorganic particles, naturally occurring organic polymeric materials, synthetic or modified naturally occurring organic polymers, vitreous materials, plastics that are intrinsically hydrophilic or modified to be hydrophilic by the presence of hydrophilic functional groups, and mixtures thereof.

5. The method of claim 1 wherein the hydrophobic matrix comprises a polymeric material selected from the group consisting of a silicone, polyvinyl butyral, polyolefin, natural or synthetic rubber, fluorinated polymer, acrylate, epoxy, and combinations thereof.

6. The method of claim 5 wherein the hydrophobic matrix comprises an adhesive.

7. The method of claim 6 wherein the adhesive is a pressure sensitive adhesive.

8. The method of claim 1 wherein the biological sample mixture is a nucleic acid sequencing reaction mixture.

9. The method of claim 8 wherein the small negatively charged organic molecules are selected from the group consisting of dye-labeled terminators, primers, degraded dye molecules, deoxynucleotide triphosphates, and mixtures thereof.

10. The method of claim 9 wherein the small negatively charged organic molecules comprise dye-labeled terminators.

11. The method of claim 10 wherein the dye-labeled terminators are selected from the group consisting of dideoxynucleotide triphosphates, dideoxynucleotide diphosphates, dideoxynucleotide monophosphates, dideoxynucleosides, and combinations thereof.

12. The method of claim 9 wherein contacting the biological sample mixture with the solid-phase extraction material is carried out under conditions effective to remove substantially all the dye-labeled terminators from the biological sample mixture.

13. The method of claim 1 wherein the biological sample mixture is a PCR reaction mixture.

14. The method of claim 13 wherein the small negatively charged organic molecules are selected from the group consisting of primers, degraded dye molecules, deoxynucleotide triphosphates, and mixtures thereof.

15. The method of claim 14 wherein contacting the biological sample mixture with the solid-phase extraction material is carried out under conditions effective to remove substantially all the primers from the biological sample mixture.

16. The method of claim 1 wherein the small negatively charged organic molecules have a molecular weight of less than about 6,000.

17. The method of claim 1 wherein the device is a microfluidic device.

18. The method of claim 1 wherein contacting the biological sample mixture with the solid-phase extraction material comprises agitating while contacting.

19. A method of removing small negatively charged organic molecules from a biological sample mixture, the method comprising:

providing a device comprising a plurality of process arrays, wherein each process array of the plurality of process arrays comprises:

a plurality of process chambers, each of the process chambers defining a volume for containing a biological sample mixture; and at least one distribution channel connecting the plurality of process chambers of the array; wherein at least one of the process arrays comprises, within the array, a solid-phase extraction material comprising solid hydrophilic particles disposed on a layer of a hydrophobic matrix and partially embedded therein, and further wherein the solid hydrophilic particles comprise molecules different than the hydrophobic matrix;

providing a biological sample mixture; and contacting the biological sample mixture with the solid-phase extraction material to remove at least a portion of the small negatively charged organic molecules from the biological sample mixture.

20. The method of claim 19 wherein the particles are disposed on the layer of hydrophobic matrix at a density of about 0.1 mg per 12 $mm^2$ surface area to about 5 mg per 12 $mm^2$ surface area.

21. The method of claim 19 wherein the layer of hydrophobic material comprises a layer of an adhesive.

22. The method of claim 21 wherein the layer of an adhesive comprises a layer of a pressure sensitive adhesive.

23. The method of claim 19 wherein the device is a microfluidic device.

24. The method of claim 19 wherein contacting the biological sample mixture with the solid-phase extraction material comprises agitating while contacting.

25. A method of removing small negatively charged organic molecules from a biological sample mixture, the method comprising:

providing a device comprising a plurality of process arrays, wherein each process array of the plurality of process arrays comprises:

a plurality of process chambers, each of the process chambers defining a volume for containing a biological sample mixture; and at least one distribution channel connecting the plurality of process chambers of the array; wherein at least one of the process arrays comprises, within the array, a solid-phase extraction material comprising solid hydrophilic particles of a hydrophilic solid support partially embedded within a hydrophobic matrix, and further wherein the solid hydrophilic particles comprise molecules different than the hydrophobic matrix;

providing a biological sample mixture; and contacting the biological sample mixture with the solid-phase extraction material to remove at least a portion of the small negatively charged organic molecules from the biological sample mixture;

wherein the biological sample mixture comprises a nucleic acid amplification reaction mixture.

26. The method of claim 25 wherein the device is a microfluidic device.

27. A method of removing small negatively charged organic molecules from a biological sample mixture, the method comprising:
   providing a device comprising a plurality of process arrays, wherein each process array of the plurality of process arrays comprises:
      a plurality of process chambers, each of the process chambers defining a volume for containing a biological sample mixture; and
      at least one distribution channel connecting the plurality of process chambers of the array; wherein at least one of the process arrays comprises, within the array, a solid-phase extraction material, wherein the solid-phase extraction material comprises solid hydrophilic particles of a hydrophilic solid support partially embedded within a hydrophobic matrix, and further wherein the solid hydrophilic particles comprise molecules different than the hydrophobic matrix;
   providing a biological sample mixture in the at least one process array; and
   transferring the biological sample mixture within the at least one process array, wherein the biological sample mixture and the solid-phase extraction material remain in contact for a sufficient time to remove at least a portion of the small negatively charged organic molecules from the biological sample mixture.

28. The method of claim 27 wherein the particles have an average particle size of at least about 5 nm.

29. The method of claim 28 wherein the particles have an average particle size of no greater than about 500 microns.

30. The method of claim 27 wherein the particles of hydrophilic solid support comprise a material selected from the group consisting of inorganic particles, naturally occurring organic polymeric materials, synthetic or modified naturally occurring organic polymers, vitreous materials, plastics that are intrinsically hydrophilic or modified to be hydrophilic by the presence of hydrophilic functional groups, and mixtures thereof.

31. The method of claim 27 wherein the hydrophobic matrix comprises a polymeric material selected from the group consisting of a silicone, polyvinyl butyral, polyolefin, natural or synthetic rubber, fluorinated polymer, acrylate, epoxy, and combinations thereof.

32. The method of claim 27 wherein the hydrophobic matrix comprises an adhesive.

33. The method of claim 32 wherein the adhesive is a pressure sensitive adhesive.

34. The method of claim 27 wherein the biological sample mixture is a nucleic acid sequencing reaction mixture.

35. The method of claim 34 wherein the small negatively charged organic molecules are selected from the group consisting of dye-labeled terminators, primers, degraded dye molecules, deoxynucleotide triphosphates, and mixtures thereof.

36. The method of claim 34 wherein the small negatively charged organic molecules comprise dye-labeled terminators.

37. The method of claim 36 wherein the dye-labeled terminators are selected from the group consisting of dideoxynucleotide triphosphates, dideoxynucleotide diphosphates, dideoxynucleotide monophosphates, dideoxynucleosides, and combinations thereof.

38. The method of claim 36 wherein the biological sample mixture with the solid-phase extraction material are contacted under conditions effective to remove substantially all the dye-labeled terminators from the biological sample mixture.

39. The method of claim 27 wherein the biological sample mixture is a PCR reaction mixture.

40. The method of claim 39 wherein the small negatively charged organic molecules are selected from the group consisting of primers, degraded dye molecules, deoxynucleotide triphosphates, and mixtures thereof.

41. The method of claim 40 wherein the biological sample mixture and the solid-phase extraction material are contacted under conditions effective to remove substantially all the primers from the biological sample mixture.

42. The method of claim 27 wherein the small negatively charged organic molecules have a molecular weight of less than about 6,000.

43. The method of claim 27 wherein the biological sample mixture and the solid-phase extraction material are agitated while in contact.

44. The method of claim 27 wherein the at least one process array comprises a loading chamber and at least one process chamber.

45. A method of removing small negatively charged organic molecules from a biological sample mixture, the method comprising:
   providing a device comprising a plurality of process arrays, wherein each process array of the plurality of process arrays comprises:
      a plurality of process chambers, each of the process chambers defining a volume for containing a biological sample mixture; and
      at least one distribution channel connecting the plurality of process chambers of the array; wherein at least one of the process arrays comprises, within the array, a solid-phase extraction material, wherein the solid-phase extraction material comprises solid hydrophilic particles disposed on a layer of a hydrophobic matrix and partially embedded therein, and further wherein the solid hydrophilic particles comprise molecules different than the hydrophobic matrix;
   providing a biological sample mixture in the at least one process array; and
   transferring the biological sample mixture within the at least one process array, wherein the biological sample mixture and the solid-phase extraction material remain in contact for a sufficient time to remove at least a portion of the small negatively charged organic molecules from the biological sample mixture.

46. The method of claim 45 wherein the biological sample mixture comprises a nucleic acid amplification reaction mixture.

47. The method of claim 45 wherein the biological sample mixture and the solid-phase extraction material are agitated while in contact.

48. A device comprising:
   a plurality of process arrays, wherein each process array of the plurality of process arrays comprises:
      a plurality of process chambers, each of the process chambers defining a volume for containing a biological sample mixture; and
      at least one distribution channel connecting the plurality of process chambers of the array;
   wherein at least one of the process arrays comprises a solid-phase extraction material within the array;
   wherein the solid-phase extraction material comprises solid hydrophilic particles of a hydrophilic solid support partially embedded within a hydrophobic matrix, and further wherein the solid hydrophilic particles comprise molecules different than the hydrophobic matrix; and wherein the device is operable to remove small negatively charged organic molecules from the biological sample mixture.

49. The device of claim 48 further comprising a plurality of valves, wherein at least one of the valves is located along the at least one distribution channel.

50. The device of claim 48 wherein the plurality of process arrays comprises a plurality of independent process arrays.

51. The device of claim 48 wherein the plurality of process arrays are arranged radially on the device.

52. The device of claim 48 wherein the hydrophobic matrix comprises an adhesive.

53. The device of claim 52 wherein the particles of hydrophilic solid support are pattern coated on a layer of the hydrophobic matrix.

54. The device of claim 48 wherein the particles of hydrophilic solid support have an average particle size of at least about 5 nm.

55. The device of claim 48 wherein the particles of hydrophilic solid support have an average particle size of no greater than about 500 microns.

56. The device of claim 48 wherein the particles of hydrophilic solid support comprise a material selected from the group consisting of inorganic particles, naturally occurring organic polymeric materials, synthetic or modified naturally occurring organic polymers, vitreous materials, plastics that are intrinsically hydrophilic or modified to be hydrophilic by the presence of hydrophilic functional groups, and mixtures thereof.

57. The device of claim 48 wherein the hydrophobic matrix comprises a polymeric material selected from the group consisting of a silicone, polyvinyl butyral, polyolefin, natural or synthetic rubber, fluorinated polymer, acrylate, epoxy, and combinations thereof.

58. The device of claim 48 wherein the hydrophobic matrix comprises an adhesive.

59. The device of claim 58 wherein the adhesive is a pressure sensitive adhesive.

60. The device of claim 48 wherein the device is a microfluidic device.

61. A device comprising:

a plurality of process arrays, wherein each process array of the plurality of process arrays comprises:

a plurality of process chambers, each of the process chambers defining a volume for containing a biological sample mixture; and at least one distribution channel connecting the plurality of process chambers of the array;

wherein at least one of the process arrays comprises a solid-phase extraction material within the array;

wherein the solid-phase extraction material comprises solid hydrophilic particles disposed on a layer of a hydrophobic matrix and partially embedded therein, and further wherein the solid hydrophilic particles comprise molecules different than the hydrophobic matrix; and wherein the device is operable to remove small negatively charged organic molecules from the biological sample mixture.

62. The device of claim 61 wherein the solid hydrophilic particles comprise a material selected from the group consisting of inorganic particles, naturally occurring organic polymeric materials, synthetic or modified naturally occurring organic polymers, vitreous materials, plastics that are intrinsically hydrophilic or modified to be hydrophilic by the presence of hydrophilic functional groups, and mixtures thereof.

63. The device of claim 61 wherein the hydrophobic matrix comprises a polymeric material selected from the group consisting of a silicone, polyvinyl butyral, polyolefin, natural or synthetic rubber, fluorinated polymer, acrylate, epoxy, and combinations thereof.

64. The device of claim 63 wherein the solid hydrophilic particles comprise a material selected from the group consisting of inorganic particles, naturally occurring organic polymeric materials, synthetic or modified naturally occurring organic polymers, vitreous materials, plastics that are intrinsically hydrophilic or modified to be hydrophilic by the presence of hydrophilic functional groups, and mixtures thereof.

* * * * *

UNITED STATES PATENT AND TRADEMARK OFFICE
CERTIFICATE OF CORRECTION

PATENT NO. : 7,347,976 B2 Page 1 of 1
APPLICATION NO. : 10/027226
DATED : March 25, 2008
INVENTOR(S) : Ranjani V. Parthasarathy It is certified that error appears in the above-identified patent and that said Letters Patent is hereby corrected as shown below:

Column 10
Line 17, delete "labled" and insert -- labeled --, therefor.

Column 12
Line 50, after "METHODS" delete "METHODS" (Second Occurrence).

Column 13
Line 25, after "METHODS" delete "METHODS" (Second Occurrence).
Line 25, delete "U.S." and insert -- (U.S. --, therefor.
Line 26, before "Bedingham" insert -- ( --.

Column 16
Line 20, after "METHODS" delete "METHODS" (Second Occurrence).

Column 18
Line 17, after "(mm)" insert -- ) --.

Column 19
Line 62, delete "Aumina" and insert -- Alumina --, therefor.

Signed and Sealed this

Twenty-ninth Day of July, 2008

JON W. DUDAS
*Director of the United States Patent and Trademark Office*